United States Patent
Omura et al.

(10) Patent No.: US 6,841,163 B2
(45) Date of Patent: Jan. 11, 2005

(54) HIGH INTERNAL AQUEOUS PHASE WATER-IN-OIL TYPE EMULSION COSMETIC COMPOSITION

(75) Inventors: Takayuki Omura, Yokohama (JP); Tomiyuki Nanba, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 10/106,847

(22) Filed: Mar. 27, 2002

(65) Prior Publication Data

US 2003/0064046 A1 Apr. 3, 2003

Related U.S. Application Data

(63) Continuation of application No. 09/597,543, filed on Jun. 19, 2000, now abandoned.

(30) Foreign Application Priority Data

Jun. 21, 1999 (JP) ............................................ 11-173509
Feb. 7, 2000 (JP) ....................................... 2000-029805

(51) Int. Cl.$^7$ .......................... A61K 6/00; A61K 7/00; A61K 31/74; A61K 31/695; A01N 55/00
(52) U.S. Cl. ..................... 424/401; 424/78.03; 514/63; 514/937; 528/10; 556/400; 556/430
(58) Field of Search ............................. 424/401, 78.02; 514/63, 722, 724, 873, 937; 528/10; 556/400, 430

(56) References Cited

U.S. PATENT DOCUMENTS

| | | | |
|---|---|---|---|
| 5,015,469 A | * | 5/1991 | Yoneyama et al. ............ 424/59 |
| 5,061,481 A | | 10/1991 | Suzuki et al. |
| 5,236,986 A | * | 8/1993 | Sakuta ........................ 524/267 |
| 5,412,004 A | | 5/1995 | Tachibana et al. |
| 5,475,126 A | | 12/1995 | Yoshida et al. |
| 5,589,165 A | | 12/1996 | Yoshida et al. |
| 5,770,112 A | | 6/1998 | Omura et al. |
| 5,776,444 A | | 7/1998 | Birtwistle et al. |
| 5,830,486 A | | 11/1998 | Nanba et al. |
| 5,853,711 A | | 12/1998 | Nakamura et al. |
| 5,990,059 A | | 11/1999 | Finel et al. |
| 6,139,851 A | | 10/2000 | Omura et al. |
| 6,156,805 A | | 12/2000 | Smith et al. |
| 6,210,690 B1 | * | 4/2001 | Nabeshima et al. ........ 424/401 |

FOREIGN PATENT DOCUMENTS

| | | |
|---|---|---|
| JP | 3-79669 | 4/1991 |
| JP | 5178733 | 7/1993 |
| JP | 9-227332 | 9/1997 |
| JP | 10-72328 | 3/1998 |
| JP | 2000-34221 | 2/2000 |
| JP | 2000-86490 | 3/2000 |

OTHER PUBLICATIONS

Translation of JP 3–79669, Suzuki et al., Apr. 4, 1991.*
KSG Series, KSG 15–16–18–21–31–32–33, "Shin–Etsu Silicone Product–Files for Cosmetics & Toiletries," ©Shin–Etsu '99.1/200.10,pp. 1–12.

* cited by examiner

*Primary Examiner*—Sreeni Padmanabhan
*Assistant Examiner*—Gregory W Mitchell
(74) *Attorney, Agent, or Firm*—Foley & Lardner LLP

(57) ABSTRACT

A high internal aqueous phase water-in-oil type emulsion cosmetic composition comprising a cross-linkable polyether-modified silicone in an amount of 0.1 to 10.0% by weight and a water-soluble polymer having a weight average molecular weight of 2000 to 300,000, an inorganic salt and an amino acid salt or a polyether-modified silicone, and having a content of an aqueous phase component of at least 50% by weight.

13 Claims, No Drawings

HIGH INTERNAL AQUEOUS PHASE WATER-IN-OIL TYPE EMULSION COSMETIC COMPOSITION

This application is a continuation of U.S. patent application Ser. No. 09/597,543, filed Jun. 19, 2000 (abandoned).

BACKGROUND OF THE INVENTION

1. Field of the Invention

The present invention relates to a high internal aqueous phase water-in-oil type emulsion cosmetic composition superior in useability and stability, in particular superior in feeling of change of aqueous phase. More specifically, the present invention relates to a high internal aqueous phase water-in-oil type emulsion cosmetic composition containing at least 50.0% by weight of an aqueous phase component and superior in useability, that is, when applied to hair or the skin, instantaneously changing in aqueous phase, superior in feeling of release of water, giving moisture to the hair or skin, having a damp feel, free from stickiness, light in spreadability and superior in stability, that is, superior in the stability with the elapse of time and superior in the stability to physical stimulus.

2. Description of the Related Art

In general, an emulsifying agent is used to make a water-in-oil type (W/O) type emulsion cosmetic composition having water dispersed in the oil of the continuous aqueous phase. As such an emulsifying agent, in the past, a glyceryl fatty acid ester, sorbitan aliphatic acid ester, or other polyhydric alcohol fatty acid ester-based surfactants or polyoxyalkylene-modified organosiloxane-based surfactants has been generally used.

Generally, in a high internal aqueous phase W/O type emulsion containing more than 50% by weight of water in the composition, however, at low temperatures, the continuous oil phase easily separates due to flocculation of drops of water. Conversely, at high temperatures, the drops of water combine to cause particles to increase and precipitate and the top portion to become only an oily component for easy separation of the oil phase again. Various proposals have already been made to reduce this instability due to temperature by formulating in large amounts of waxes to increase the consistency, but even these have been insufficient in that there was incomplete stability at high temperatures. Further, since W/O type emulsions have oil components as external phases, they are advantageous in protecting the skin or imparting softness, but suffer from problems in useability such as stickiness at the time of use, heaviness in spreadability, and hardness.

It is desirable to select and blend a preferable oil ingredient from a broad range from polar oils to nonpolar oils with a high internal phase ratio, but it was not possible to obtain a stable water-in-oil type emulsion cosmetic composition of a system including a polar oil using a conventional polyol fatty acid ester-based activant or of a system including a nonpolar oil with a polyoxyalkylene-modified organopolysiloxane-based active agent. Therefore, there were restrictions on the selection of the oil component in conventional water-in-oil type emulsion cosmetic compositions and, it was impossible to achieve broader based popularity due to the feeling in the application.

To eliminate these problems in useability and stability, a composition is sought which has a high internal aqueous phase ratio, which, when applied onto the skin or hair, has emulsion particles break down instantaneously simultaneous with the application and release the water in the internal aqueous phase, and which is excellent in the stability with the elapse of time. However, at the present time, while it is possible to use the polyol fatty acid ester-based surfactants or polyoxyalkylene-modified organopolysiloxane-based surfactants which had been used as W/O type emulsifying agents in the past so as to prepare a high internal aqueous phase W/O type emulsion cosmetic composition, the problem in the area of the stability with the elapse of time cannot be solved.

Among these, a paste-like polyether-modified silicone composition obtained by processing the cross-linkable polyether-modified silicone of the structural formula (I) or (II) used in the present invention with silicone oil has recently been developed. The technique of producing a water-in-oil type emulsion composition superior in the stability with the elapse of time and application feeling using this composition has already been proposed. Further, a water-in-oil type emulsion composition improved in useability by formulating in a large amount of water has been proposed. Inclusion of silicic acid anhydride or hydrophobic silica to keep the stability with the elapse of time has also already been proposed (Japanese Unexamined Patent Publication (Kokai) No. 6-40847).

It is desirable that such a water-in-oil type emulsion composition have stability for the pipeline transport required for continuous production in addition to the aforesaid properties, that is, the useability and stability, or stability in use when repeatedly extruded for use, but if physical stimulus is given, such as in a vibration test or tube squeezing test to confirm it, there has been the problem that the emulsion is broken down and the internal aqueous phase component is released even with a composition produced by the proposed methods.

SUMMARY OF THE INVENTION

Accordingly, the objects of the present invention are to eliminate the above-mentioned problems of the prior art and to provide a high internal aqueous phase water-in-oil type emulsion cosmetic composition giving moistness to the skin or hair, having a damp feel, free from stickiness, light in spreadability, and superior in the stability with the elapse of time, that is, superior in useability and stability.

Another object of the present invention is to provide a high internal aqueous phase water-in-oil type emulsion cosmetic composition which is superior in useability, that is, which, when applied onto the hair or skin, instantaneously changes in aqueous phase, is superior in feeling of release of water, gives moistness to the hair or skin, has a damp feel, is free from stickiness, and further is superior in the stability with the elapse of time and superior in the stability when applying physical stimulus such as in a tube squeezing test.

Other objects and advantages of the present invention will be apparent from the following description.

In accordance with the present invention, there is provided a high internal aqueous phase water-in-oil type emulsion cosmetic composition comprising the following component (A) in an amount of 0.1 to 10.0% by weight and the following component (B) and having a content of an aqueous phase component of at least 50% by weight:

(A) at least one cross-linkable polyether-modified silicone having the formula (I):

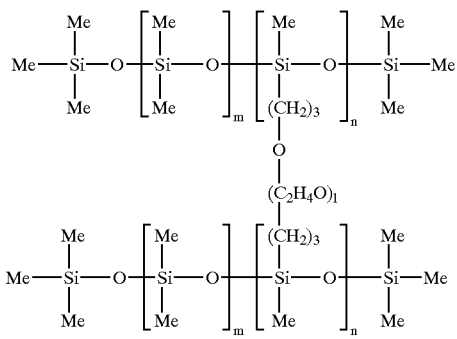

(I)

wherein 1 is 3–20, m is 10–200, n is 1.0–10.0, and (B) at least one useability improver selected from the group consisting of water-soluble polymers having a weight average molecular weight of 2000 to 300,000, inorganic salts and amino acid salts.

In accordance with the present invention, there is also provided a high internal aqueous phase water-in-oil type emulsion cosmetic composition comprising the following component (A') in an amount of 0.1 to 10.0% by weight and the following component (B') and having a content of an aqueous phase component of at least 50% by weight:

(A') at least one cross-linkable polyether-modified silicone having the formula (II):

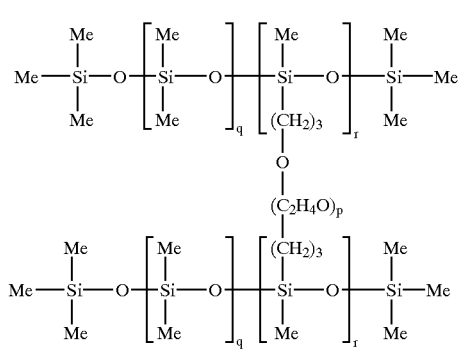

(II)

wherein p is 3 to 20, q is 10 to 200, and r is 1.0 to 10.0, and (B) at least one polyether-modified silicone having the formula (III):

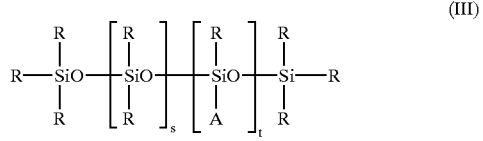

(III)

wherein A is a polyoxyalkylene group having the formula: $-C_3H_6O(C_2H_4O)_a(C_3H_6O)_bR'$, wherein. R' is a hydrogen atom or a group selected from the group consisting of an acyl group and $C_1$ to $C_4$ alkyl group, a is 5 to 50, and b is 5 to 50, R is a methyl group or phenyl group, s is 301 to 1000, and t is 1 to 40.

DESCRIPTION OF THE PREFERRED EMBODIMENTS

The present inventors engaged in intensive research on high internal aqueous phase water-in-oil type emulsion cosmetic compositions. Under these conditions, taking note of the characteristics of cross-linkable polyether-modified silicone or paste-like polyether-modified silicone compositions, they tried to produce a high internal aqueous phase water-in-oil type emulsion cosmetic composition using the same and superior in useability and stability. As a result, we found that a high internal aqueous phase water-in-oil type emulsion cosmetic composition obtained by using a paste-like polyether-modified silicone composition, as an emulsifying agent, could not give sufficient characteristics of useability, that is, giving moistness to the hair or skin, having a damp feel, free of stickiness, and light in spreadability. The inventors engaged in further research and found that using both the above emulsifying agent, in particular, a cross-linkable polyether-modified silicone, and a specific component to improve useability so as to form a water-in-oil type emulsion cosmetic composition, it is possible to stably emulsify a broad range of oil components from polar oils to nonpolar oils such as triglyceride, ester oils, and hydrocarbon oils and form a high internal aqueous phase water-in-oil type emulsion cosmetic composition having a content of the aqueous phase component of at least 50.0% by weight giving moistness to the skin or hair, having a damp feel, free from stickiness, light in spreadability, and excellent in the stability with the elapse of time.

The high internal aqueous phase water-in-oil type emulsion cosmetic composition according to the first aspect of the present invention was developed under the above circumstances.

Thus, in the first aspect of the present invention, by use of this composition, it is possible to provide a high internal aqueous phase water-in-oil type emulsion cosmetic composition which has the outstanding characteristics of giving moistness to the hair or skin, having a damp feel, free from stickiness, light in spreadability, and superior in the stability with the elapse of time.

The inventors further engaged in intensive research on high internal aqueous phase water-in-oil type emulsion cosmetic compositions. Taking note of the characteristics of cross-linkable polyether-modified silicone or paste-like polyether-modified silicone compositions, we tried to produce a high internal aqueous phase water-in-oil type emulsion cosmetic composition using the same and superior in useability, that is, which, when applied onto the hair or skin, instantaneously changes in aqueous phase, is superior in feeling of release of water, and is superior in stability, in particular, the stability with the elapse of time as well as stability against physical stimulus such as in a tube squeezing test.

As a result, we found that by formulating the above cross-linkable polyether-modified silicone or paste-like polyether-modified silicone composition and formulating the above specific polyether-modified silicone, it is possible to produce a high internal aqueous phase water-in-oil type emulsion cosmetic composition which, when applied onto the hair or skin, instantaneously changes in aqueous phase, is superior in feeling of release of water, gives moistness to the hair or skin, a damp feel, no stickiness, and further is superior in the stability with the elapse of time as well as stability against physical stimulus, whereby the present invention was completed.

Note that Japanese Unexamined Patent Publication (Kokai) No. 3-79669 discloses a specific example of use of both the cross-linkable polyether-modified silicone used in the present invention and a low polymerized compound of the structural formula (III) where s=5 to 300, but this low polymerized compound is lower in polymerization degree than the polyether-modified silicone of the structural formula (III) where s=301 to 1000 used in the present invention. This is outside the range used in the present invention. In this case, while this is superior in stability, it is not sufficient in feeling of release of water, that is, the feeling of a change in aqueous phase.

The high internal aqueous phase water-in-oil type emulsion cosmetic composition superior in useability and stability of the second aspect of the present invention was developed in view of the above situation.

Further, in the second aspect of the present invention, by use of this composition, it is possible to provide a high internal aqueous phase water-in-oil type emulsion cosmetic composition which, when applied onto the hair or skin, instantaneously changes in aqueous phase, is superior in feeling of release of water, gives moistness to the hair or skin, a damp feel, no stickiness, and is superior in the stability with the elapse of time and stability against physical stimulus. Note that "change of aqueous phase" means the feeling of a change from a cream to water. This is one of the useful items in the design of a water-in-oil type emulsion cosmetic composition in view of reduction of stickiness, imparting moistness to the skin or hair, etc. in terms of useability.

Further, the stability with the elapse of time and stability against physical stimulus here mean not only stability of the emulsion composition as in the past, which was considered a problem when a cosmetic composition was placed at a high temperature or low temperature or other special temperature, but also stability when physical stimulus is applied in a tube squeezing test etc.

The embodiments of the first aspect of the present invention will now be explained.

The high internal aqueous phase water-in-oil type emulsion cosmetic composition of the present invention means a water-in-oil (W/O) type emulsion cosmetic composition having a content of an aqueous phase component of at least 50.0% by weight, preferably 60% to 85% by weight, in the total composition and having the aqueous phase component dispersed in the continuous oil phase component. As specific cosmetic compositions, there are, for example, an emulsion, skin cream, hair cream, liquid foundation, eyeliner, mascara, eyeshadow, and other liquid emulsion or cream products, but the cosmetic composition of the present invention is not limited to these. Any of the above water-in-oil type emulsion cosmetic compositions correspond to the cosmetic composition of the present invention.

The cross-linkable polyether-modified silicone used in the first aspect of the present invention is a polymer obtained by cross-linking a methyl hydrogen polysiloxane with diallyl polyether at the two ends. It may be produced by the method described in, for example, Japanese Unexamined Patent Publication (Kokai) No. 4-272932 or Japanese Unexamined Patent Publication (Kokai) No. 5-140320 etc. The present invention may use those produced by these methods or commercially available products.

The cross-linkable polyether-modified silicone used in the present invention is preferably a paste-like polyether-modified silicone composition obtained by mixing the same with silicone oil under shear force, but the polyether-modified silicone and silicone oil etc. may also be formulated, as cosmetic composition components. The polyether-modified silicone and silicone oil etc. may, in some cases, be mixed after the other cosmetic composition components were formulated.

In using the cross-linkage polyether-modified silicone of the structural formula (I) in the present invention, 1 is preferably 3 to 20. If less than 3, outside this range, the paste-like composition obtained by mixing the cross-linkable polyether-modified silicone and silicone oil under a shear force is poor in the emulsificability of water, while if more than 20, the swelling in silicone oil becomes no longer sufficient, and therefore these are not preferred. Further, m is preferably 10 to 200. If less than 10, there is insufficient swelling with respect to silicone oil, while if more than 200, the paste-like composition obtained by mixing thereof with silicone oil under a shear force becomes poor in emulsificability of water.

Further, n is preferably 1.0 to 10.0. If less than 1.0, a three-dimensional structure cannot be formed, a paste-like composition is not obtained even if mixing with silicone oil, and the emulsificability of water becomes inferior as well. Conversely, if more than 10, the cross-linking density of the three-dimensional structure becomes too high, and therefore, even if mixed with silicone oil, the silicone oil cannot be retained and a stable paste-like composition cannot be obtained, and therefore, this is not preferred.

In the first aspect of the present invention, the silicone oil to be mixed with the cross-linkable polyether-modified silicone is not particularly limited. It may be a linear or branched type. Various types of silicone oil may be used, but a low viscosity silicone oil having a viscosity at 25° C. of not more than 100 mPa·s may be preferably used. Examples of the specific silicone oil usable in the present invention are methyl polysiloxane, methylphenyl polysiloxane, ethyl polysiloxane, ethylmethyl polysiloxane, ethylphenyl polysiloxane, octamethyl cyclotetrasiloxane, decamethyl cyclopentasiloxane, or other cyclic dimethyl polysiloxanes etc. These may be used alone or in any combination thereof.

The ratio of the cross-linkable polyether-modified silicone and silicone oil in the present invention may be 10 to 1000 parts by weight of silicone oil, preferably 20 to 500 parts by weight, to 100 parts by weight of cross-linkage polyether-modified silicone as mentioned above. If the amount of the cross-linkable polyether-modified silicone is smaller than the above range, a stable, excellent gel structure cannot be maintained. Contrary to this, if more than the above range, the composition feels heavy on the skin or is poor in the useability, etc. The device for performing the mixing under a shear force is also not particularly limited. Any device conventionally used may be used. For example, a triple roll mill, twin roll mill, sand grinder, colloid mill, Gaulin homogenizer, etc. may be mentioned, but in particular a triple roll mill may be preferably used.

Regarding the amount of the cross-linkable polyether-modified silicone used as an emulsifying agent in the present invention formulated into the cosmetic composition, 0.1 to 10.0% by weight may be mixed based upon the total weight of the cosmetic composition. If less than 0.1% by weight, outside of the range, the aqueous phase component of more than 50.0% by weight of the inner aqueous phase cannot be emulsified. Contrary to this, if more than 10.0% by weight, the spreadability is poor and the useability becomes heavy. When the cross-linkable polyether-modified silicone is formulated as a paste-like polyether-modified silicone composition, the amount formulated should be selected so as to give an amount formulated of cross-linkable polyester-modified silicone in the above range.

As the oil phase component formulated into the high internal aqueous phase water-in-oil type emulsion cosmetic composition of the present invention, it is possible to use any oil agent usually formulated into a water-in-oil type (W/O) type emulsion cosmetic composition, that is, oil phase component, without particular restriction. Any natural animal or plant oil or synthetic oil may be used. Examples of the oil phase component are specifically liquid paraffin, squalane, or other liquid, paste, or solid hydrocarbon, wax, higher aliphatic acid, higher alcohol, ester, glyceride, or dimethyl polysiloxane or polyether-modified, fluorine-modified, or other various modified silicones or other silicone-based oils etc.

Further, in the emulsion cosmetic composition of the present invention, the above oil phase component is formulated into the cosmetic composition in a range of 10% by weight to 50% by weight based upon the total weight of the cosmetic composition. If less than 10% by weight, it is difficult to make the cosmetic composition a water-in-oil type. Contrary to this, if more than 50% by weight, the water in the internal aqueous phase becomes too sparse and there is an insufficient feeling of moistness in terms of the useability. Note that, as an oil corresponding to "good" in the W/O type emulsion cosmetic composition, there are natural animal and plant oils, synthetic oils, and all other oily components contained in cosmetic compositions. The emulsifying agent, that is, the cross-linkable polyether-modified silicone, and its preferable mode, that is, the paste-like polyether-modified silicone composition are also oily components and are components corresponding to "good".

The water or other aqueous phase component formulated together with the oil phase components in the high internal aqueous phase water-in-oil type emulsion cosmetic composition of the present invention, that is, the "W", is water, ethanol, a thickening agent, or other water-soluble compound. The water-soluble polymer, inorganic salt, and amino acid salt formulated as an agent for improving applicability, or useability are also aqueous phase components and correspond to the "W" in the present invention. The amount of the aqueous phase component formulated, in the present invention, is 50% by weight to less than 90% by weight based upon the total weight of the cosmetic composition. The amount formulated is water itself and may be at least 60% by weight. By doing this, it is possible to give a feeling of moisture, and therefore this is preferable. With an amount of the aqueous phase component of less than 50% by weight, the characteristic of water content is not easily manifested and the feeling of moistness is insufficient. Conversely, if formulated an amount of 90% by weight or more, it becomes difficult to obtain a water-in-oil type cosmetic composition.

Next, the components formulated as agents for improving useability in the present invention will be alluded to. One or more components formulated as agents for improving useability are selected from water-soluble polymers having a weight average molecular weight of 2000 to 300,000, preferably 3,000 to 20,000, inorganic salts, and amino acid salts as explained above. Therefore, as the agent for improving useability, it is sufficient to use one or more types of the above water-soluble polymers, inorganic salts, and/or amino acid salts. It is also possible to use two or more types of inorganic salts or amino acid salts mixed together. Further, the amount formulated has to be in a range bringing out the performance in improving useability. The amounts of the compounds of the useability improvers are as given below.

Examples of the water-soluble polymer are polyethylene glycol, polyvinyl alcohol, polyacrylic acid, carboxymethyl cellulose, polyvinyl pyrrolidone, hydroxymethyl cellulose, methyl cellulose, and other water-soluble synthesized polymers and dextrin, peptin, alginic acid, chondroitin sulfate, and other natural water-soluble polymers etc.

The weight average molecular weight of the water-soluble polymer is 2000 to 300,000, preferably 3000 to 100,000. The polymer having a molecular weight of less than 2000 does not contribute to improvement of the useability. Further, if the molecular weight is more than 300,000, there is little contribution to the improvement of the useability and stickiness is caused in the feeling of application of the emulsion cosmetic composition. The amount formulated is 0.1 to 20.0% by weight, preferably 0.2 to 10.0% by weight, based upon the total weight of the emulsion cosmetic composition. If less than 0.1% by weight, the useability cannot be improved. Contrary to this, if more than 20.0% by weight, this becomes a cause of stickiness when used as an emulsion cosmetic composition.

Particularly preferred among water-soluble polymers is polyethylene glycol. It is particularly effective to improve the useability of the emulsion cosmetic composition compared with others and has the advantage of a good feeling of application when used as an emulsion cosmetic composition. A particularly preferred molecular weight in the polyethylene glycol is 3000 to 20,000. The amount formulated is preferably 1 to 10.0% by weight based upon the total weight of the emulsion cosmetic composition.

Examples of the inorganic salts usable in the present invention are hydrochloric acid, sulfuric acid, nitric acid, carbonic acid, phosphoric acid, and other alkali metal salts, alkali earth metal salts, aluminum salts, zinc salts, ammonium salts, etc. Examples of the preferable inorganic salts are sodium chloride, potassium chloride, magnesium chloride, calcium chloride, aluminum chloride, zinc chloride, ammonium chloride, or other chlorides, sodium sulfate, potassium sulfate, magnesium sulfate, aluminum sulfate, zinc sulfate, ammonium sulfate, and other sulfates, sodium nitrate, potassium nitrate, magnesium nitrate, calcium nitrate, aluminum nitrate, zinc nitrate, ammonium nitrate, and other nitrates, sodium carbonate, potassium carbonate, magnesium carbonate, calcium carbonate, and other carbonates, and sodium phosphate, potassium phosphate, and other phosphates.

Among these, as inorganic salts, sodium chloride, potassium chloride, magnesium chloride, calcium chloride, aluminum chloride, sodium sulfate, potassium sulfate, magnesium sulfate, and aluminum sulfate are particularly preferred. The amount of the inorganic salt formulated as an agent for improving the useability in the present invention is 0.1 to 8.0% by weight, preferably 0.2 to 5.0% by weight. If less than 0.1% by weight, the useability of the emulsion cannot be improved, while even if formulated more than 8.0% by weight, the effect is not enhanced.

The amino acid salt formulated, as an useability improving useability in the present invention is one with the carboxyl group or amino group in the amino acid forming a salt. The water-soluble amino acid salt used is not particularly limited. For example, there are sodium aspartate, potassium aspartate, magnesium aspartate, calcium aspartate, sodium glutamate, potassium glutamate, magnesium glutamate, calcium glutamate, glutamic acid hydrochloride, cysteine hydrochloride, histidine hydrochloride, lysine hydrochloride, ornithine hydrochloride, ornithine acetate, tryptophan hydrochloride, alginin-glutamate, orthinine-glutamate, lysine-glutamate, lysine-asparagate, ornithine-asparagate, etc.

Among these, as amino acid salts, sodium glutamate is preferred. The amount of the amino acid salt formulated when using the same as a stabilizer in the present invention is 0.1 to 8.0% by weight, preferably 0.2 to 5.0% by weight, based upon the total weight of the emulsion cosmetic composition. If less than 0.1% by weight, the useability cannot be improved. Contrary to this, if more than 8.0% by weight, the effect is not enhanced.

In the emulsion cosmetic composition of the present invention, in addition to the above essential components, it is of course also possible to contain a water-soluble component (i.e., aqueous phase component) and oil-soluble component (i.e., oil phase component) normally formulated into emulsion cosmetic compositions. These include, for example, humectants, preservatives, antioxidants, ultraviolet absorbers, beauty components, fragrances, fragrance retainers, thickeners, coloring pigments, glittering pigments, organic powder, hydrophobic ally-treated pigments, tar dyes, etc. These may be formulated to a range not detracting from the effect of the present invention.

As specific cosmetic compositions of the high internal aqueous phase water-in-oil type emulsion cosmetic composition of the present invention, as explained above, there are an emulsion, skin cream, hair cream, liquid foundation, eyeliner, mascara, eyeshadow, and other emulsion or cream products. These products may be manufactured by an ordinary method using the above essential components and components ordinarily formulated into cosmetic compositions.

The detailed explanation of the second aspect of the present invention will now be given only as the embodiments thereof, but of course the present invention is not limited in any way thereto.

The high internal aqueous phase water-in-oil type emulsion cosmetic composition according to the second aspect of the present invention means a water-in-oil type (W/O) type emulsion cosmetic composition having a content of the aqueous phase component of at least 50.0% by weight in the total components and having the aqueous phase component dispersed in the continuous oil phase component.

Examples of the specific forms of the cosmetic composition are an emulsion, skin cream, hair cream, liquid foundation, eyeliner, mascara, eyeshadow, and other liquid emulsions or cream-like products, but the cosmetic composition of the present invention is not limited thereto. Any of the above water-in-oil type emulsion cosmetic compositions correspond to the cosmetic composition of the present invention.

The cross-linkable polyether-modified silicone used in the present invention is a polymer obtained by cross-linking a methyl hydrogen polysiloxane with the diallyl polyether at the two ends. It may be produced by the method described in, for example, Japanese Unexamined Patent Publication (Kokai) No. 4-272932 or Japanese Unexamined Patent Publication (Kokai) No. 5-140320 etc. The present invention may use the polyether-modified silicone produced by these methods or a commercially available product.

The cross-linkable polyether-modified silicone used is preferably made a paste-like polyether-modified silicone composition obtained by mixing this with silicone oil under a shear force, but the cross-linkable polyether-modified silicone and silicone oil etc. may also be formulated, as cosmetic components. For example, the cross-linkable polyether-modified silicone and silicone oil etc. may in some cases be mixed after the other cosmetic composition components as well have been formulated.

In using the cross-linkable polyether-modified siicone of the structural formula (II) in the present invention, p is preferably 3 to 20. If less than 3, outside this range, the paste-like composition obtained by mixing the cross-linkable polyether-modified silicone and silicone oil is poor in the emulsifiability of water. Contrary to this, if more than 20, the swelling in silicone oil becomes no longer sufficient, and therefore these are not preferred. Further, q is preferably 10 to 200. If less than 10, there is insufficient swelling with respect to silicone oil. Contrary to this, if more than 200, the paste-like polyether-modified silicone composition obtained by mixing with silicone oil under a shear force becomes poor in emulsifiability of water.

Further, r is preferably 1.0 to 10.00. If less than 1.0, a three-dimensional structure cannot be formed, a paste-like composition is not obtained even if mixing with silicone oil, and the emulsifiability of water becomes inferior as well. Conversely, if more than 10, the cross-linking density of the three-dimensional structure becomes too high, and therefore, even if mixing with silicone oil, the silicone oil cannot be retained and a stable paste-like composition cannot be obtained, and therefore, this is not preferred.

In the second aspect of the present invention, the silicone oil to be mixed with the cross-linkable polyether-modified silicone is not particularly limited. It may be a linear or branched type. Various types of silicone oil may be used, but a low viscosity silicone oil having a viscosity at 25° C. of not more than 100 mPa·s may be preferably used.

Examples of the specific silicone oil used, methyl polysiloxane, methylphenyl polysiloxane, ethyl polysiloxane, ethylmethyl polysiloxane, ethylphenyl polysiloxane, octamethyl cyclotetrasiloxane, decamethyl cyclopentasiloxane, or other cyclic dimethyl polysiloxanes etc. These may be used alone or in any combination thereof.

The ratio of the cross-linkable polyether-modified silicone and silicone oil in the present invention may be 10 to 1000 parts by weight of silicone oil, preferably 20 to 500 parts by weight, to 100 parts by weight of cross-linkable polyether-modified silicone. If the amount of the cross-linkable polyether-modified silicone is smaller than the above range, a stable, excellent gel structure cannot be maintained. Contrary to this, if more than the above range, the composition feels heavy on the skin (that is, lacks suitable spreadability at the time of coating) or is poor in useability (i.e., feeling in the application thereof) etc.

Regarding the amount of the cross-linkable polyether-modified silicone used in the present invention formulated into the cosmetic composition, 0.1 to 10.0% by weight may be formulated based upon the total weight of the cosmetic composition. If less than 0.1% by weight, outside of the range, the aqueous phase component of more than 50.0% by weight of the inner aqueous phase cannot be emulsified. Contrary to this, if more than 10.0% by weight, the spreadability is poor and the useability becomes heavy.

When the cross-linkable polyether-modified silicone is formulated as a paste-like polyether-modified silicone composition, the amount formulated should be selected so as to give an amount formulated of cross-linkable polyester-modified silicone in the above range. Note that the apparatus for mixing under shear force used when forming the paste-like polyether-modified silicone composition is not particularly limited. Any apparatus normally used may be used. For example, a triple roll mill may be preferably used.

In the emulsion cosmetic composition of the present invention, in addition to the above essential components, it is of course possible to formulate an oil usually formulated into an emulsion cosmetic composition. Further, in addition to the above component (A'), it is possible to use a natural animal or plant oil or synthetic oil. Examples of such an oil are specifically liquid paraffin, squalane, or other liquid, paste, or solid hydrocarbon, wax, higher aliphatic acid, higher alcohol, ester, glyceride, silicone-based oil, etc.

Further, in this emulsion cosmetic composition, the above oil phase component was formulated into the cosmetic composition in a range of 10% to 50% by weight, based upon the total weight of the cosmetic composition. If less than 10% by weight, it is difficult to make the cosmetic composition a water-in-oil type, while if more than 50% by weight, the internal aqueous phase water becomes too sparse and there is an insufficient feeling of moistness in terms of useability. Note that, as an component corresponding to "good" in the W/O type emulsion cosmetic composition, there are natural animal and plant oils, synthetic oils, and all other oily components usually contained in cosmetic compositions. The cross-linkable polyether-modified silicone composition, an essential component in the present invention, and diester, triester, etc. liquid at room temperature also therefore are corresponding oil phase components.

The water or other aqueous phase component formulated together with the oil phase component in the high internal aqueous phase component water-in-oil type emulsion cosmetic composition of the present invention, that is, the "W", is water, ethanol, a thickening agent, or other water-soluble compound. Regarding the amount of the aqueous phase component formulated, in the present invention, the component is formulated by a range of 50% by weight to less than 90% by weight based upon the total weight of the cosmetic composition. The amount formulated may be at least 60% by weight as water itself. By doing this, it is possible to give a feeling of moistness, and therefore, this is preferable. With an amount of the aqueous phase component of less than 50% by weight, the characteristic of water content is not easily manifested and the feeling of moistness is insufficient. Conversely, if formulated in an amount of 90% by weight or more, it becomes difficult to obtain a water-in-oil type cosmetic composition.

Next, the polyether-modified silicone of the component (B'), another essential component of the emulsion cosmetic composition of the present invention, will be explained. The polyether-modified silicones usable in the present invention are those represented by the above formula (III) and may be used alone or in any combination thereof.

Examples of the acyl group indicated by R' in the formula (III) are, specifically, a formyl group, acetyl group, propionyl group, butyryl group, acryloyl group, benzoyl group, toluoyl group, etc. Examples of the $C_1$ to $C_4$ alkyl group are, specifically, a methyl group, ethyl group, i-propyl group, n-propyl group, t-butyl group, n-butyl group, etc.

When a or b is less than 5 in the polyoxyalkylene group of the above formula (III), the polyether-modified silicone no longer exhibits a sufficient surfactant effect. Conversely, when more than 50, the composition obtained has a sticky feeling. The content of the polyoxyalkylene group in the molecule of the formula (III) (that is, the polyether-modified silicone of structural formula (III)) is not particularly limited, but the content of the polyoxyalkylene group is preferably over 20% by weight of the entire molecular weight. This is because, when the content of the polyoxyalkylene group is less than 20% by weight, the emulsifiability of the polyether-modified silicone is remarkably decreased.

Further, s is 301 to 1000, while t is 1 to 40. When m is less than 300 and t is less than 1, the emulsion stability becomes poor. Further, when s is more than 50 and less than 300 and t is 1 to 40, conversely the emulsion stability becomes too good and the characteristic feeling of change of aqueous phase of the present invention cannot be obtained. When s is more than 1000 and t is more than 40, the composition obtained has a sticky feeling. Further, m:n is preferably 200:1 to 5:1, more preferably 60:1 to 15:1.

The weight average molecular weight and the viscosity at 25° C. of the polyether-modified silicone usable in the present invention are not particularly limited, but to form a stable emulsion and give a satiny feel, a viscosity of the polyether-modified silicone when made a 50% by weight solution of octamethyl tetrasiloxane or isoparaffin in the range of 1000 to 100,000 mPa·s is particularly preferred.

The amount of the polyether-modified silicone formulated in the present invention is 0.01 to less than 5.0% by weight, more preferably 0.05 to 3.0% by weight. In the composition of the present invention, if the amount of the polyester-modified silicone is less than 0.01% by weight, stable emulsion is difficult and the emulsion breaks down in a vibration test or tube squeezing test. That is, the stability during pipeline transport during mass production or the stability during repeated extrusion for use can no longer be expected. Conversely, if more than 5.0% by weight, the emulsion stability becomes too good and the characteristic feeling of change of aqueous phase of the present invention, where a cream turns into water, is lost and the composition gives rise to a sticky feeling.

In the emulsion cosmetic composition of the present invention, in addition to the above essential components, it is of course also possible to include water-soluble components and oil-soluble components generally formulated into emulsion cosmetic compositions. This include, for example, humectants, preservatives, antioxidants, ultraviolet absorbers, beauty components, fragrances, fragrance retainers, thickeners, coloring pigments, glittering pigments, organic powder, hydrophobic ally treated pigments, tar dyes, etc. These may be formulated up to a range not detracting from the effect of the present invention.

As specific forms of the high internal aqueous phase water-in-oil type emulsion cosmetic composition of the present invention, as explained above, there are an emulsion, skin cream, hair cream, liquid foundation, eyeliner, mascara, eyeshadow, and other emulsion or cream products. These products may be manufactured by an ordinary method using the above essential components and components ordinarily formulated into cosmetic compositions.

EXAMPLES

The present invention will now be further illustrated by, but is by no means limited to, the following Examples and comparative Examples.

Compositions and Performance Tests of Hair Treatments of Examples and Comparative Examples High internal aqueous phase water-in-oil type emulsion hair treatments were produced as Examples I-1 to I-4 of compositions corresponding to the present invention and Comparative Examples I-1 and I-2 of compositions not corresponding to the present invention. The treatments obtained were tested for stability and tested for useability and evaluated for performance. The stability was tested by observation of the appearance after allowing the compositions to stand at 50° C. for 1 hour, while the useability was tested by a test of actual use by a panel of female experts (10). The test of actual use judged whether the cosmetic composition was to the panelists' liking according to the evaluation criteria. The compositions and test results of Examples I-1 to I-4 and Comparative Examples I-1 and I-2 are shown in Table I-1.

Note that in Table I-1, the amounts of the components formulated are all expressed as % by weight. Therefore, looking at the amounts of the aqueous phase components and oil phase components of the hair treatments in the Table, for example, in Example I-1, the aqueous phase components are water, ethanol, sodium glutamate, and paraben, and therefore the total amount is 87.0% by weight. Since the oil phase components are dimethyl polysiloxane and the paste-like polyether-modified silicon composition, the amount of the oil phase components is 13.0% by weight.

The evaluation criteria in the performance test were as follows:

Evaluation Criteria for Stability

Good: No separation at all seen

Fair: Almost no separation seen

Poor: Separation of liquid phase (oil phase or aqueous phase)

Evaluation Criteria for Useability (Used Coated on Hair) Feeling of Stickiness

V.Good: All 10 panelists judge there is moistness, dampness, no stickiness, and excellent useability.

Good: Seven to nine panelists judge there is glossiness, moistness, no stickiness, and excellent use.

Fair: Three to six panelists judge there is glossiness, moistness, no stickiness, and excellent use.

Poor: Two or fewer panelists judge there is glossiness, moistness, no stickiness, and excellent use.

Spreadability

V.Good: All 10 panelists judge spreadability is light and smooth and useability excellent Good: Seven to nine panelists judge spreadability is light and smooth and useability excellent Fair: Three to six panelists judge spreadability is light and smooth and useability excellent Poor: Two or fewer panelists judge spreadability is light and smooth and useability excellent The paste-like polyether-modified silicone composition used in the tests was as follows. That is, as the cross-linkable polyether-modified silicone, the compound having the formula (I) wherein l, m, and n were respectively l=5 to 15, m=20 to 100, and n=1.2 to 5 was used. 100 parts by weight of the modified silicone and 400 parts by weight of methyl polysiloxane having a viscosity of 6 mPa·s were mixed together under a shear force to make a paste.

Process of Production of Hair Treatment

The process of production of the hair treatments of Examples I-1 to I-4 and Comparative Examples I-1 and I-2 used in the performance tests was as follows:

Process of Production of Hair Treatments of Examples I-1 to I-4 and Comparative Example I-1

(1) and (3) were mixed. While stirring the mixed oil solution by a high speed agitator (dispersion mixer), a mixed aqueous solution of (7), (8), and (12) in which is dissolved (9), (10), or (11) is gradually added thereto at room temperature to obtain the desired W/O type emulsion hair treatment.

ated by all 10 of the panelists as having moistness, having a damp feel, free from stickiness, light in spreadability, and excellent in useability. Further, they can be understood to be superior in stability as well.

As opposed to this, the hair treatment of Comparative Example I-1 not containing any water-soluble polymer, inorganic salt, and amino acid salt was evaluated as poor in non-stickiness and spreadability by the panelists—the lowest evaluation. Further, the hair treatment of Comparative Example I-2 containing sodium glutamate and polyethylene glycol, agents for improving the useability, but not containing a paste-like polyether-modified silicone composition was evaluated as fair in non-stickiness and spreadability and poor in useability—the lowest evaluation.

From the results of the above performance tests, it is clear that the high internal aqueous phase water-in-oil type hair treatments of the present invention are good in both non-stickiness and spreadability and superior in useability and further are superior in stability and that the high internal aqueous phase water-in-oil type emulsion cosmetic composition of the present invention is a cosmetic composition superior in useability and stability.

TABLE I-1

|  | Examples | | | | Comp. Examples | |
| --- | --- | --- | --- | --- | --- | --- |
|  | I-1 | I-2 | I-3 | I-4 | I-1 | I-2 |
| (1) Dimethyl polysiloxane (20 mPa · s) | 10.0 | 10.0 | 10.0 | 10.0 | 10.0 | 5.0 |
| (2) Squalane | — | — | — | — | — | 5.0 |
| (3) Paste-like polyether-modified silicone composition | 3.0 | 3.0 | 3.0 | 3.0 | 3.0 | — |
| (4) Sucrose eruca acid ester (product name: Ryoto Sugar Ester ER-190, made by Mitsubishi Chemical Foods) | — | — | — | — | — | 0.35 |
| (5) Sucrose eruca acid ester (product name: Ryoto Sugar Ester ER-290, made by Mitsubishi Chemical Foods) | — | — | — | — | — | 0.35 |
| (6) Sucrose oleic acid ester (product name: Ryoto Sugar Ester O-170, made by Mitsubishi Chemical Foods) | — | — | — | — | — | 0.30 |
| (7) Ion exchanged water | 80.85 | 80.85 | 80.85 | 80.85 | 81.85 | 82.85 |
| (8) Ethanol | 5.0 | 5.0 | 5.0 | 5.0 | 5.0 | 5.0 |
| (9) Sodium glutamate | 1.0 | — | — | 0.5 | — | 1.0 |
| (10) Potassium chloride | — | 1.0 | — | — | — | — |
| (11) Polyethylene glycol (molecular weight 6000) | — | — | 1.0 | 0.5 | — | — |
| (12) Paraben | 0.15 | 0.15 | 0.15 | 0.15 | 0.15 | 0.15 |
| Test Results |  |  |  |  |  |  |
| Stability | Good | Good | Good | Good | Good | Poor |
| Useability (feeling of stickiness) | V. Good | V. Good | V. Good | V. Good | Poor | Fair |
| Useability (spreadability) | V. Good | V. Good | V. Good | V. Good | Poor | Fair |

Process of Production of Hair Treatment of Comparative Example I-2

(1), (2), and (4) to (6) were warmed to 70° C. and homogeneously dissolved. Next, while stirring the homogeneously dissolved oil phase by a high speed agitator (dispersion mixer), an aqueous phase of (7), (8), (9), and (12) warmed to 70° C. and homogeneously dissolved was gradually added thereto at room temperature to obtain the desired W/O type emulsion hair treatment.

Results of Performance Tests

The results of the performance tests of Examples I-1 to I-4 and Comparative Examples I-1 and I-2 were as shown in Table I-1. According to this, the hair treatments of Examples I-1 to I-4 of the present invention containing water-soluble polymers, inorganic salts, and amino acid salts were evalu- Example I-5

Skin Cream

| Component | Amount (% by weight) |
| --- | --- |
| (1) Liquid paraffin | 6.0 |
| (2) Decamethyl cyclopentasiloxane | 10.0 |
| (3) 1,3-butylene glycol | 3.0 |
| (4) Paste-like polyether-modified silicone composition*1 | 2.5 |
| (5) Ion exchanged water | 72.1 |
| (6) Sodium chloride | 3.0 |

-continued

| Component | Amount (% by weight) |
|---|---|
| (7) Paraben | 0.2 |
| (8) Antioxidant | 0.1 |
| (9) Ethanol | 3.0 |
| (10) Fragrance | 0.1 |

*[1]obtained by mixing 100 parts by weight of cross-linkable polyether-modified silicone of the formula (I) where l, m, and n are l = 3 to 10, m = 50, and n = 2.5 to 4 with 500 parts by weight of decamethyl cyclopentasiloxane under shear force.

Process of Production and Performance of Product (1), (2), and (4) were mixed to prepare an oil phase mixture in advance. Next, while stirring this oil phase mixture using a high speed agitator, a mixed aqueous phase obtained by mixing, stirring, and dissolving (3) and (5) to (10) was gradually added at room temperature to obtain the desired skin cream.

The cream obtained had a very good useability in the same way as Examples I-1 to I-4. That is, when applied onto the skin, it gave moistness, a damp feel, no stickiness, and was light in spreadability. Further, the stability was good.

Example I-6

Hair Styling Cream

| Component | Amount (% by weight) |
|---|---|
| (1) Isoparaffin | 3.0 |
| (2) Dimethyl polysiloxane (500 mPa · s) | 5.0 |
| (3) Glycerin | 5.0 |
| (4) Paste-like polyether-modified silicone composition (same as Examples I-1 to I-4) | 1.5 |
| (5) Paste-like polyether-modified silicone composition*[1] | 1.5 |
| (6) Acryl resin alkanolamine solution (product name: Plus Size L-53P, GOO Chemical) | 3.0 |
| (7) Ion exchanged water | 70.8 |
| (8) Ethanol | 8.0 |
| (9) Polyethylene glycol (molecular weight 10,000) | 2.0 |
| (10) Paraben | 0.1 |
| (11) Fragrance | 0.1 |

*[1]obtained by mixing 100 parts by weight of cross-linkable polyether-modified silicone of the formula (I) where l, m, and n are l = 10, m = 30 to 70, and n = 3 to 5 with 300 parts by weight of methylphenyl polysiloxane under shear force.

Process of Production and Performance of Product (1), (2), (4), and (5) were mixed to prepare an oil phase mixture in advance. Next, while stirring this oil phase mixture using a high speed agitator, an aqueous phase mixture obtained by mixing and stirring (3) and (6) to (11) to dissolve was gradually added at room temperature to obtain the desired hair styling cream.

The hair styling cream thus obtained had a very good useability. That is, when applied onto the skin, it gave moistness, a damp feel, no stickiness, and was light in spreadability. Further, the stability was good.

Example I-7

W/O Type Emulsion Foundation

| Component | Amount (% by weight) |
|---|---|
| (1) Squalane | 1.0 |
| (2) Dimethyl polysiloxane (6 mPa · s) | 3.0 |
| (3) Propylene glycol | 2.5 |
| (4) Paste-like polyether-modified silicone composition*[1] | 3.5 |
| (5) Ion exchanged water | 70.6 |
| (6) Ethanol | 1.0 |
| (7) Sodium glutamate | 1.5 |
| (8) Potassium chloride | 1.5 |
| (9) Paraben | 0.1 |
| (10) Dextrin palmitate treated titanium dioxide | 5.0 |
| (11) Dextrin palmitate treated mica | 5.0 |
| (12) Dextrin palmitate treated talc | 2.5 |
| (13) Dextrin palmitate treated iron oxide | 2.5 |
| (14) Antioxidant | 0.1 |
| (15) Fragrance | 0.2 |

*[1]obtained by mixing 100 parts by weight of cross-linkable polyether-modified silicone of the formula (I) where l, m, and n are l = 7, m = 50, and n = 40 with 250 parts by weight of octamethyl cyclotetrasiloxane under shear force.

Process of Production and Performance of Product (1), (2), (4), and (10) to (13) were mixed to disperse and prepare an oil phase dispersion in advance. Next, while stirring this oil phase dispersion using a high speed agitator (dispersion mixer), an aqueous phase mixture obtained by dissolving (3), (5) to (9), (14), and (15) was gradually added at room temperature to obtain the desired W/O type emulsion foundation.

The W/O type emulsion foundation obtained had a very good useability. That is, when applied onto the skin, it gave moistness, a damp feel, no stickiness, and was light in spreadability.

As clear from the explanation of the above Examples I-1 to I-7 and embodiments of the invention etc., the present invention provides a high internal aqueous phase water-in-oil type emulsion cosmetic composition using as an emulsifying agent a cross-linkable polyether-modified silicone, in particular a paste-like polyether-modified silicone composition containing the same mixed with silicone oil under a shear force, and using, as an agent for improving useability, one or a combination of two or more components selected from water-soluble polymers having a weight average molecular weight of 2000 to 300,000, inorganic salts, and an amino acid salts. As a result, as clear from the explanation of the above Examples I-1 to I-7 and embodiments of the present invention etc., the cosmetic composition of the present invention gives moistness to the skin or hair, a damp feel, no stickiness, and is light in spreadability and therefore superior in useability and further is superior in the stability with the elapse of time, and therefore, exhibits outstanding effects.

Examples II-1 to II-4 and Comparative Examples II-1 to II-5

High internal aqueous phase water-in-oil type emulsion skin creams of Examples II-1 to II-4 of compositions corresponding to the present invention and Comparative Examples II-1 to II-5 of compositions not corresponding to the present invention were produced. The skin creams obtained were tested for actual use and evaluated in performance by a stability test and a panel of female experts (10).

The stability was tested by observation of the appearance after allowing the composition to stand at 50° C. for one month and by packing the composition in a plastic tube, conducting a squeezing test (using an apparatus squeezing a tube 20 times a minute so as to repeatedly squeeze a tube for 30 minutes), then observing the appearance to confirm the stability. Further, the test of actual application judged whether the cosmetic composition was to the panelists' liking according to the following evaluation criteria.

The compositions of the skin creams of the Examples and Comparative Examples used in the tests and the test results were as shown in Table II-1. Note that the amounts of the components formulated are all given in % by weight.

modified silicone having the above formula (II) wherein p, q, and r are p=5 to 15, q=20 to 100, and r=1.2 to 5 and mixing 100 parts by weight of the modified silicone with 400 parts by weight of methyl polysiloxane having a viscosity of 6 mPa·s under a shear force.

Further, the polyether-modified silicone compositions used in the tests were 50% solutions of decamethyl cyclopentasiloxane having the following formulae (IV) to (VII):

TABLE II-1

|  | Examples | | | | Comparative Examples | | | | |
| --- | --- | --- | --- | --- | --- | --- | --- | --- | --- |
|  | II-1 | II-2 | II-3 | II-4 | II-1 | II-2 | II-3 | II-4 | II-5 |
| (1) Dimethyl polysiloxane (10 mPa·s) | 10.0 | 10.0 | 10.0 | 10.0 | 10.0 | 10.0 | 10.0 | 10.0 | 10.0 |
| (2) Squalane | 3.0 | 3.0 | 3.0 | 3.0 | 3.0 | 3.0 | 3.0 | 3.0 | 3.0 |
| (3) Paste-like polyether-modified silicone composition | 1.0 | 5.0 | 0.5 | 8.0 | 5.0 | 12.0 | 5.0 | 5.0 | 5.0 |
| (4) Composition of polyether-modified silicone (III) | 0.1 | 0.5 | 3.0 | 0.01 | — | 0.001 | — | — | — |
| (5) Composition of polyether-modified silicone (IV) | — | — | — | — | — | — | 0.5 | — | — |
| (6) Composition of polyether-modified silicone (V) | — | — | — | — | — | — | — | 0.5 | — |
| (7) Composition of polyether-modified silicone (VI) | — | — | — | — | — | — | — | — | 0.5 |
| (8) Ion exchanged water | 72.7 | 68.3 | 70.3 | 65.79 | 68.8 | 68.799 | 68.3 | 68.3 | 68.3 |
| (9) Ethanol | 10.0 | 10.0 | 10.0 | 10.0 | 10.0 | 10.0 | 10.0 | 10.0 | 10.0 |
| (10) Sodium glutamate | 3.0 | 3.0 | 3.0 | 3.0 | 3.0 | 3.0 | 3.0 | 3.0 | 3.0 |
| (11) Paraben | 0.2 | 0.2 | 0.2 | 0.2 | 0.2 | 0.2 | 0.2 | 0.2 | 0.2 |
| Test Results | | | | | | | | | |
| Stability (50° C., after 1 M) | Good | Good | Good | Good | Good | Good | Good | Good | Fair |
| Stability (tube squeezing test) | Good | Good | Good | Good | Poor | Good | Good | Good | Fair |
| Useability (feeling of change of phase) | Good | Good | Good | Good | Good | Poor | Poor | Good | Good |
| Useability (sticky feel) | Good | Good | Good | Good | Good | Fair | Good | Poor | Good |

The evaluation criteria in the performance tests were as follows:

Evaluation Criteria for Stability

Good: No separation at all seen

Fair: Almost no separation seen

Poor: Separation of liquid phase (oil phase or aqueous phase)

Evaluation Criteria for Useability (Used Coated on Skin)

Feeling of Release of Water (Feeling of Change of Phase)

Good: Instantaneous change in phase judged

Fair: Change in phase judged

Poor: Change in phase not felt judged

Useability

Good: At least seven panelists judged moistness, dampness, no sticky feeling, and good feeling in use Fair: Three to less than seven panelists judged moistness, dampness, no sticky feeling, and good feeling in use Poor: Two or less panelists judged moistness, dampness, no sticky feeling, and good feeling in use.

The paste-like polyether-modified silicone composition used in the tests was as follows. That is, it was a paste-like composition obtained by using a cross-linkable polyether-

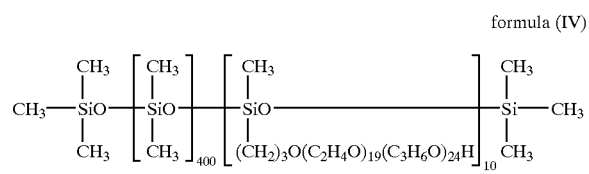

formula (IV)

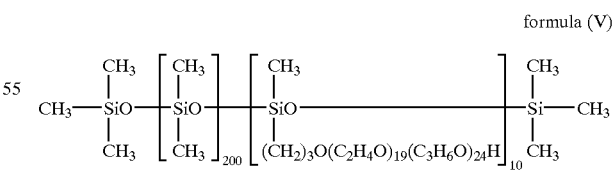

formula (V)

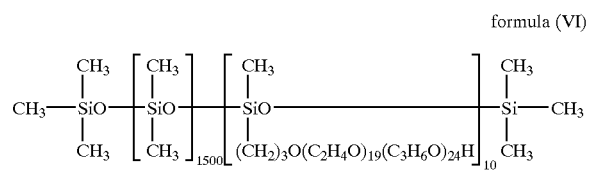

formula (VI)

formula (VII)

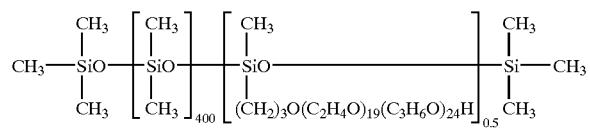

The process of production of the skin creams of Examples II-1 to II-4 and Comparative Examples II-1 to II-5 used in the performance tests was as follows:

Process of Production of Skin Creams of Examples II-1 to II-4 and Comparative Examples II-1 to II-5

(1) to (7) were mixed to form an oil solution. While stirring the mixed oil solution by a high speed agitator (dispersion mixer), the aqueous phase of (8) to (11) was gradually added at room temperature to obtain the desired W/O type emulsion skin cream.

Results of Performance Tests

The results of the above performance tests were as follows. The skin creams of Examples II-1 to II-4 were excellent in useability and stability. That is, when applied onto the skin, they gave an instantaneous feeling of change of phase, were superior in feeling of release of water, gave moistness to the hair, had a damp feel, and were free from stickiness. Further, regarding stability, not only did they not suffer from separation of the oil and water after storage at 50° C. for one month, but also the results of the tube squeezing test were excellent. The results show that it is possible to avoid separation of oil and water during pipeline transport during mass production and achieve stability at the time of repeated extrusion and use.

Further, the skin creams of the Comparative Examples were inferior in stability, feeling of change of phase, and useability. Specifically, Comparative Example II-1 was superior in feeling of change of phase, but since the emulsifying agent was only cross-linkable polyether-modified silicone, while no separation at all was seen at 50° C. after one month, separation occurred in the tube squeezing test. Comparative Examples II-2. and II-3 were excellent in stability, but inferior in feeling of change of phase. Comparative Example II-4 was excellent in stability and feeling of change of phase, but was sticky. Comparative Example II-5 was superior in feeling of change of phase, but inferior in stability.

Example II-6

Body Cream

| Component | Amount (% by weight) |
|---|---|
| (1) Dimethyl polysiloxane (6 mPa · s) | 10.0 |
| (2) Decamethyl cyclopentasiloxane | 6.0 |
| (3) 1,3-butylene glycol | 3.0 |
| (4) Paste-like polyether-modified silicone composition*1 | 2.5 |
| (5) 50% solution of octamethyl cyclotetrasiloxane of polyether-modified silicone composition having the formula (VIII) | 2.5 |
| (6) Ion exchanged water | 72.6 |
| (7) Paraben | 0.2 |
| (8) Antioxidant | 0.1 |
| (9) Ethanol | 3.0 |
| (10) Fragrance | 0.1 |

*1 obtained by mixing 100 parts by weight of cross-linkable polyether-modified silicone of the formula (II) where p, q, and r are p = 3 to 10, q = 50, and r = 2.5 to 4 with 500 parts by weight of decamethyl cyclopentasiloxane under shear force formula (VIII)

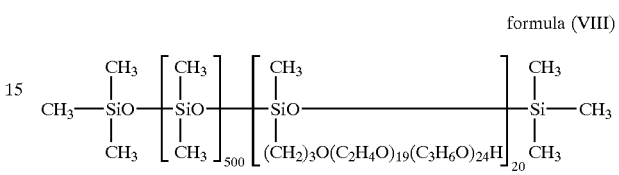

Process of Production and Performance of Product (1), (2), (4), and (5) were mixed to prepare an oil phase mixture in advance. Next, while stirring this oil-phase mixture using a high speed agitator, an aqueous phase mixture obtained by mixing and stirring (3) and (6) to (10) to dissolve was gradually added at room temperature to obtain the desired body cream. The body cream obtained had a good useability in the same way as Examples II-1 to II-4. That is, when applied onto the skin, it released water instantaneously, gave moistness, a damp feel, and further no stickiness. Further, the stability with the elapse of time and the results of the tube squeezing test were also excellent.

Example II-7

Hair Styling Cream

| Component | Amount (% by weight) |
|---|---|
| (1) Dimethyl polysiloxane (100 mPa · s) | 15.0 |
| (2) Glycerin | 5.0 |
| (3) Paste-like polyether-modified silicone composition (same as Examples 1 to 4) | 1.5 |
| (4) Paste-like polyether-modified silicone composition*1 | 1.5 |
| (5) 50% isoparaffin solution of octamethyl cyclotetrasiloxane of polyether-modified silicone composition having the structural formula (IX) | 4.0 |
| (6) Acryl resin alkanolamine solution (product name: Plus Size L-53P, GOO Chemical) | 3.0 |
| (7) Ion exchanged water | 64.8 |
| (8) Ethanol | 8.0 |
| (9) Paraben | 0.1 |
| (10) Fragrance | 0.1 |

*1 obtained by mixing 100 parts by weight of cross-linkable polyether-modified silicone of the formula (I) where l, m, and n are l = 10, m = 30 to 70, and n = 3 to 5 with 300 parts by weight of methylphenyl polysiloxane under shear force formula (IX)

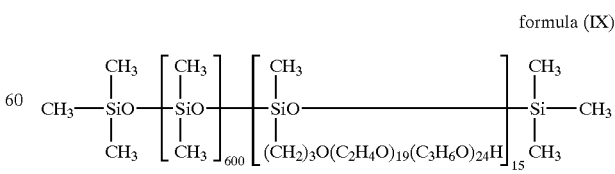

Process of Production and Performance of Product (1), (3), (4), and (5) were mixed to prepare an oil phase mixture in advance. Next, while stirring this oil-phase mixture using a high speed agitator, an aqueous phase mixture obtained by mixing and stirring (2) and (6) to (10) to dissolve was gradually added at room temperature to obtain the desired hair styling cream.

The hair styling cream thus obtained had a good useability, that is, when applied onto the hair, it released water instantaneously, gave moistness and gloss, a damp feel, and further no stickiness. Further, the stability with the elapse of time and the results of the tube squeezing test were also excellent.

Example II-8

W/O Type Emulsion Foundation

| Component | Amount (% by weight) |
|---|---|
| (1) Dimethyl polysiloxane (20 mPa · s) | 6.0 |
| (2) Propylene glycol | 2.5 |
| (3) Paste-like polyether-modified silicone composition*1 | 3.5 |
| (4) 40% solution of decamethyl cyclopentasiloxane of polyether-modified silicone composition having the formula (X) | 1.5 |
| (5) 40% solution of decamethyl cyclopentasiloxane of polyether-modified silicone composition having the formula (IV) | 1.5 |
| (5) Ion exchanged water | 77.2 |
| (6) Ethanol | 1.0 |
| (7) Paraben | 0.1 |
| (8) Dextrin palmitate treated titanium dioxide | 5.0 |
| (9) Dextrin palmitate treated mica | 2.5 |
| (10) Dextrin palmitate treated talc | 2.5 |
| (11) Dextrin palmitate treated iron oxide | 2.5 |
| (12) Antioxidant | 0.1 |
| (13) Fragrance | 0.1 |

*1 obtained by mixing 100 parts by weight of cross-linkable polyether-modified silicone of the structural formula (II) where p, q, and r are p = 7, q = 50, and r = 40 with 250 parts by weight of octamethyl cyclotetrasiloxane under shear force formula (X)

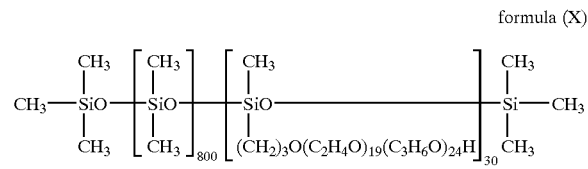

Process of Production and Performance of Product (1), (3), (4), and (8) to (11) were mixed to disperse and prepare an oil phase dispersion in advance. Next, while stirring this oil-phase dispersion using a high speed agitator (dispersion mixer), an aqueous phase mixture obtained by dissolving (2) and (5) to (13) was gradually added at room temperature to obtain the desired W/O type emulsion foundation.

The W/O type emulsion foundation thus obtained had a good useability, that is, when applied onto the skin, it instantaneously released water, gave moistness, a moist feel, and further no stickiness. Further, the stability with the elapse of time and the results of the tube squeezing test were also excellent.

As shown in Example II-1 to II-8, the present invention provides a high internal aqueous phase water-in-oil type emulsion cosmetic composition using a paste-like silicone composition obtained by mixing one or more types of cross-linkable polyether-modified silicone, in particular one or more types of cross-linkable polyether-modified silicone, with silicone oil under a shear force and further using in combination one or more types of specific polyether-modified silicones.

As a result, the cosmetic composition of the present invention provided, as clear from the above description of the Examples II-1 to II-8 and embodiments of the invention, when applied onto the hair or skin, instantaneously changes in phase, is superior in feeling of release of water, gives moistness to the hair or skin, a damp feel, no stickiness, and is superior in the stability with the elapse of time and the stability against physical stimulus. That is, it is possible to avoid separation of oil and water during pipeline transport during mass production and achieve stability at the time of repeated extrusion and use. As clear from the above, the present invention is a cosmetic composition exhibiting outstanding effects.

What is claimed is:

1. An internal aqueous phase water-in-oil emulsion cosmetic composition comprising the following component (A) in an amount of 0.1 to 10.0% by weight, the following component (B) in an amount of 0.1 to 20.0% by weight, and an aqueous phase component (C) in an amount of at least 50% by weight, each of which is based upon the total weight of the composition:

(A) at least one cross-linked polyether-modified silicone having the formula (I)

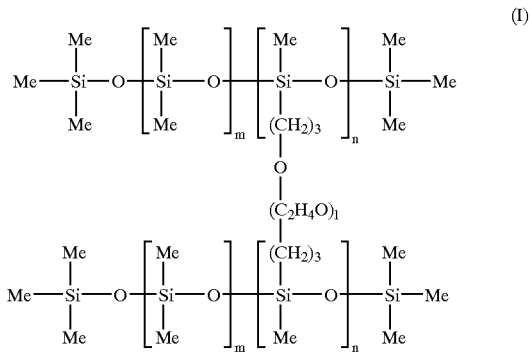

wherein 1 is 3–20, m is 10–200, n is 1.0–10.0, and (B) at least one useability improver selected from the group consisting of water-soluble polymers having a weight average molecular weight of 2000 to 300,000, and amino acid salts, wherein said water-soluble polymers are selected from the group consisting of polyethylene glycol, polyvinyl alcohol, polyacrylic acid, carboxymethyl cellulose, polyvinyl pyrrolidone, hydroxymethyl cellulose, methyl cellulose, dextrin, peptin, alginic acid, and chondroitin sulfate.

2. An internal aqueous phase water-in-oil emulsion cosmetic composition as claimed in claim 1, wherein component (A) comprises a cross-linked polyether-modified silicone and a silicone oil that are mixed together under shear force, and wherein the ratio of the cross-linked polyether-modified silicone to silicone oil is 100 parts by weight: 10 to 1000 parts by weight.

3. An internal aqueous phase water-in-oil emulsion cosmetic composition as claimed in claim 1, wherein the content of component (B) is present in 0.2 to 10.0% by weight, based upon the total weight of the composition.

4. An internal aqueous phase water-in-oil emulsion cosmetic composition as claimed in claim 1, wherein the water-soluble polymer is polyethylene glycol.

5. An internal aqueous phase water-in-oil emulsion cosmetic composition as claimed in claim 1, wherein the amino acid salt is sodium glutamate.

6. An internal aqueous phase water-in-oil emulsion cosmetic composition as claimed in claim 1, wherein component (C) is water and is present in an amount of at least 60.0% by weight, based upon the total weight of the composition.

7. An internal aqueous phase water-in-oil emulsion cosmetic composition comprising the following component (A') in an amount of 0.1 to 10.0% by weight, the following component (B') in an amount of 0.01 to 5.0% by weight, and an aqueous phase component (C') in amount of at least 50% by weight, each of which is based upon the total weight of the composition:

(A') at least one cross-linked polyether-modified silicone having the formula (II):

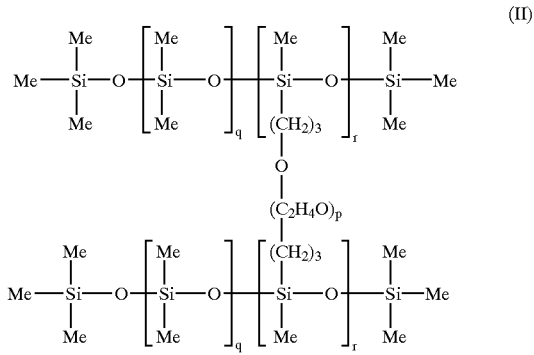

(II)

wherein p is 3 to 20, q is 10 to 200, and r is 1.0 to 10.0, and (B') at least one polyether-modified silicone having the formula (III):

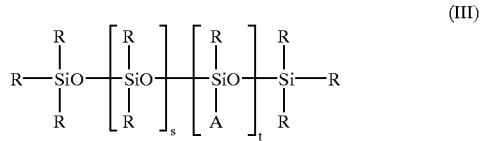

(III)

wherein A is a polyoxyalkylene group having the formula: —$C_3H_6O(C_2H_4O)_a(C_3H_6O)_b$R', wherein R' is a hydrogen atom or a group selected from the group consisting of an acyl group and a $C_1$ to $C_4$ alkyl group; a is 5 to 50; R is a methyl group or phenyl group; s is 301 to 1000; and t is 1 to 40.

8. An internal aqueous phase water-in-oil emulsion cosmetic composition as claimed in claim 7, wherein component (A') comprises a cross-linked polyether-modified silicone and a silicone oil that are mixed together under shear force, and wherein the ratio of the cross-linked polyether-modified silicone to silicone oil is 100 parts by weight: 10 to 1000 parts by weight.

9. An internal aqueous phase water-in-oil emulsion cosmetic composition as claimed in claim 7, wherein the content of component (B') is present in an amount of 0.05 to 3.0% by weight, based upon the total weight of the composition.

10. An internal aqueous phase water-in-oil emulsion cosmetic composition as claimed in claim 7, wherein the content of the aqueous phase component is at least 60% by weight, based upon the total weight of the composition.

11. A method for improving useability of an internal aqueous phase water-in-oil emulsion cosmetic composition by incorporating at least one useability improver selected from the group consisting of water-soluble polymers having a weight average molecular weight of 2000 to 300,000, inorganic salts, and amino acid salts into an internal aqueous phase water-in-oil emulsion cosmetic composition comprising the following component (A) in an amount of 0.1 to 10.0% by weight and an aqueous phase component in an amount of at least 50% by weight:

(A) at least one cross-linked polyether-modified silicone having the formula (I)

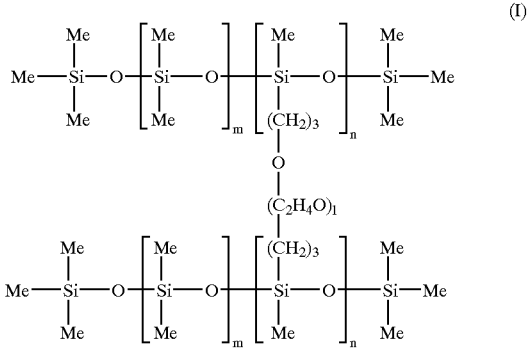

(I)

wherein 1 is 3–20, m is 10–200, and n is 1.0–10.0.

12. A method as claimed in claim 11, wherein the water-soluble polymer is polyethylene glycol.

13. A method as claimed in claim 11, wherein the amino acid salt is sodium glutamate.

* * * * *